(12) United States Patent
Takada et al.

(10) Patent No.: US 7,262,317 B2
(45) Date of Patent: Aug. 28, 2007

(54) FREEZE-DRIED PREPARATION OF N[O-(P-PIVALOYLOXYBENZENASULFONYL AMINO) BENZOYL] GLYCINE MONOSODIUM SALT TETRAHYDRATE AND PROCESS FOR PRODUCING SAME

(75) Inventors: Akira Takada, Mishima-gun (JP); Masao Sudo, Mishima-gun (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 10/333,354

(22) PCT Filed: Jul. 23, 2001

(86) PCT No.: PCT/JP01/06331

§ 371 (c)(1),
(2), (4) Date: May 22, 2003

(87) PCT Pub. No.: WO02/07724

PCT Pub. Date: Jan. 31, 2002

(65) Prior Publication Data

US 2004/0092587 A1 May 13, 2004

(30) Foreign Application Priority Data

Jul. 23, 2000 (JP) .............................. 2000-221962

(51) Int. Cl.
*C07C 315/00* (2006.01)
*C07C 303/00* (2006.01)
*C07C 317/00* (2006.01)
*A61K 31/24* (2006.01)
*A61K 31/195* (2006.01)

(52) U.S. Cl. ........................... 560/11; 560/12; 560/13; 514/540; 514/562; 562/430

(58) Field of Classification Search ................. 560/11, 560/12, 13; 562/430; 514/540, 562
See application file for complete search history.

(56) References Cited

U.S. PATENT DOCUMENTS 5,359,121 A * 10/1994 Imaki et al. .................. 560/13
6,552,082 B2 * 4/2003 Takada et al. ............... 514/562

FOREIGN PATENT DOCUMENTS

| EP | 318146 | 5/1989 |
|----|--------|--------|
| EP | 0 347 168 A | 12/1989 |
| EP | 539223 | 4/1993 |
| JP | 63-270623 | 11/1988 |
| WO | WO97/23239 | 7/1997 |

OTHER PUBLICATIONS

Patent Abstracts of Japan, Feb. 10, 1997, JP 040692 A (Ono Pharmaceutical Co., Ltd.)

* cited by examiner

*Primary Examiner*—Taylor Victor Oh
(74) *Attorney, Agent, or Firm*—Sughrue Mion, PLLC

(57) ABSTRACT

A method for the preparation of a freeze-dried product of N-[o-(p-pivaloyloxybenzenesulfonylamino)benzoyl]glycine monosodium salt tetra-hydrate dissolved in a mixed solvent of water and ethanol, and the freeze-dried product obtained by the method.

According to the present invention, N-[o-(p-pivaloyloxybenzenesulfonylamino)benzoyl]glycine monosodium salt tetra-hydrate is dissolved in a small amount of a mixed solvent of water and ethanol, and therefore it is possible to manufacture high-dosage product by freeze-drying.

1 Claim, No Drawings

US 7,262,317 B2

FREEZE-DRIED PREPARATION OF N[O-(P-PIVALOYLOXYBENZENASULFONYL AMINO) BENZOYL] GLYCINE MONOSODIUM SALT TETRAHYDRATE AND PROCESS FOR PRODUCING SAME

TECHNICAL FIELD

The present invention relates to a freeze-dried product of N-[o-(p-pivaloyloxybenzenesulfonylamino)benzoyl]glycine monosodium salt tetra-hydrate and a process for the manufacture thereof, characterized by using a mixed solvent of water and ethanol.

BACKGROUND

As to the compound used in the present invention, a free compound thereof, i.e. the compound of formula (II)

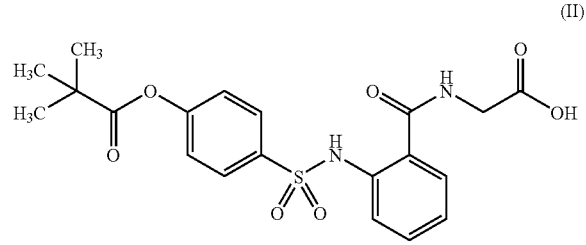

(II)

is described in example 2 (63) of JP kokai hei 3-20253 (i.e. EP 347168) and a monosodium salt tetrahydrate thereof of formula (I)

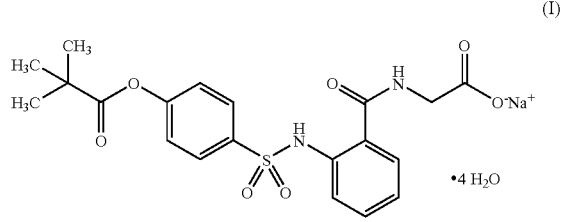

(I)

(at times abbreviated as compound (I)) is described in example 3 of JP kokai hei 5-194366 (i.e. EP 539223) and in reference example 1 of JP kokai hei 9-40692 (no EP publication).

Compound (I) has an inhibitory activity against elastase and is a very useful compound which is expected to be used for the treatment of acute pulmonary disorders. Since those patients suffering from acute pulmonary disorders are in a serious condition, it is necessary to administer a drug parenterally, preferably as an injection for a long time (from 24 hours to several days) continuously. Therefore compound (I) is appropriately formulated as an injection or a solid composition to be dissolved before administration, more preferably formulated as a freeze-dried product. And considering the convenience, a high-dosage product in a small vial compared with the amount of active ingredient is preferable.

By the way, in the manufacturing process of a freeze-dried product, generally, a drug needs to be kept in a clear solution. That is because suspension and emulsion do not give a certain concentration and may cause a problem such as blockade of nozzles of the filling equipment as well.

Considering the effective dose of compound (I) and the volume of suitable closed containers (vials, ampoules, etc.), for the manufacture of a high-dosage freeze-dried product of compound (I), the required solubility is estimated to be 80 mg/mL or more in subjecting to freeze-drying.

However, compound (I) is hardly soluble in water or ethanol; the solubility is 0.4 mg/ml in water, and 6.0 mg/ml in ethanol. Therefore, by normal solvents it is difficult to prepare a clear solution for the process of a high-dosage freeze-dried product.

JP kokai hei 9-40692 discloses a method for the preparation of compound (I) by suspending a compound of formula (II) to a mixed solvent of water and ethanol, adding an aqueous solution of sodium hydroxide thereto, heating and then cooling. This operation shows a method for the preparation of a sodium salt tetra-hydrate from a free carboxylic acid of formula (II) but does not disclose a freeze-dried product of sodium tetra-hydrate of formula (I).

JP kokai hei 5-194366 discloses a method for the preparation of freeze-dried product of compound (I) by using sodium carbonate and water, but the method does not accomplish to give a solubility of 80 mg/mL or more, which is the level which the present invention intends to overcome.

Additionally, it proved that the pH of the freeze-dried product manufactured according to the above method was ascended in the time course and may decompose compound (I), so it is not necessarily preferable.

DISCLOSURE OF THE INVENTION

The purpose of the present invention is to improve the solubility of a hardly soluble drug, i.e. compound (I) and then to provide a high-dosage freeze-dried product thereof.

As a result of energetic investigations in order to improve the solubility of compound (I) and to obtain a high-dosage freeze-dried product, surprisingly, the present inventors have found that the purpose was accomplished by adding freeze-dried product having high-dosage and to complete the present invention.

That is, the present invention relates to a product characterized by freeze-drying N-[o-(p-pivaloyl oxybenzenesulfonylamino)benzoyl]glycine monosodium salt tetra-hydrate of formula (I)

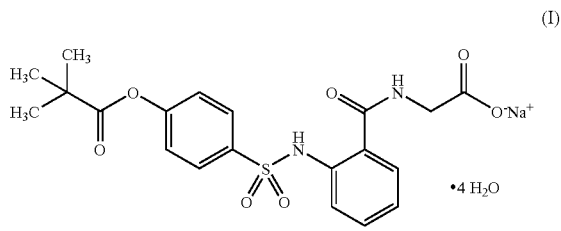

(I)

and a process for the manufacture thereof.

More particularly, the present invention relates to a freeze-dried product of N-[o-(p-pivaloyloxybenzenesulfonylamino)benzoyl]glycine monosodium salt tetra-hydrate of formula (I) using mixed solvent of water and ethanol, optionally comprising excipients and a process for the manufacture thereof.

Compound (I) has, as shown above, a very low solubility; 0.4 mg/ml in water, 6.0 mg/ml in ethanol. In order to obtain a freeze-dried product to prepare a high-dosage product of this compound, it is necessary to improve the solubility.

Hereby to prepare mixed solvent of water and ethanol in various ratios to measure the solubility, then it was found that compound (I) has a solubility of 80 mg/mL or more in a mixed solvent of ethanol and water; wherein ethanol/water=3.0/7.0~8.0/2.0 (v/v).

In the above range, compound (I) is very well dissolved and so it is possible to prepare a high dosage freeze-dried product by freeze-drying the solution.

On the other hand, the cooling capacity of normal lyophilizer is up to around −50° C. Around −50° C. the ratio of organic solvent to the total amount is over 40%, it is in danger of bumping during the freeze-drying process because the mixture is not freezed. Therefore, the amount of an organic solvent to add must be limited less than around 40% of the total solution.

Therefore, for the ratio of mixed solvent of water and ethanol, ethanol/water=3.0/7.0~4.0/6.0 is preferable, and ethanol/water=3.0/7.0~3.5/6.5 (v/v) is more preferable.

Besides, above determines the percent by volume, but it may be converted to weight by multiplying density (d). For example, when the percent by volume is converted to the percent by weight assuming the density of ethanol d=0.785 g/ml, then ethanol/water=3.0/7.0~4.0/6.0 (v/v) equals to ethanol/water=2.35/7.0~3.14/6.0 (w/w) and ethanol/water=3.0/7.0~3.5/6.5 (v/v) equals to-ethanol/water=2.35/7.0~2.75/6.5 (w/w).

Thus prepared solution according to the above composition is very dense and the freeze-dried product manufactured by the solution is very stable as shown in the following example 2.

The reconstituted solution of the freeze-dried product of the present invention is stable and it is administered via infusion after preparation of parenteral solution (see example 3 below).

Compound (I) may be prepared according to known methods (for example, described in JP 5-194366 or JP 9-40692).

The process of manufacturing a freeze-dried product of formula (I) may be carried out by known methods.

A product manufactured by freeze-drying concentrated solution, which was prepared using a mixed solvent of water and ethanol, is not known at all so far. The product is excellent in that good solubility and stability is assured not only just after the preparation but also during long storage.

The doses to be administered of compound (I) are determined depending upon age, body weight, symptom, the desired therapeutic effect, the route of administration, and the duration of the treatment. In the human adult, the doses between 100 mg and 1500 mg per person are generally administered by continuous administration between 1 and 24 hours per day from vein. Of course the doses to be used depend upon various conditions. Therefore, there are cases in which doses lower than or greater than the ranges specified above may be used.

To the product of the present invention are optionally added excipients. Preferable excipients are, lactose, glucose, maltose, mannitol, sodium chloride, etc. but in terms of freeze-dried cake, mannitol is more preferably used.

The products of the present invention may further include, stabilizing agents, pain-reducing agents, buffering agents and preserving agents, etc.

The products of the present invention are sterilized in the final process or prepared by aseptic operation. The freeze-dried products may be dissolved in sterilized distilled water for injection or other solvents (e.g. physiological saline) before use.

INDUSTRIAL APPLICABILITY

Use of mixed solvent of water and ethanol facilitates to improve the solubility of compound (I) remarkably.

Improvement of the solubility of compound (I) facilitates to prepare a solution of high density, and accordingly it is possible to increase the amount of freeze-dried product. As a result, it is possible to prepare a high-dosage product in a small vial in contrast to the amount of a product. The present invention facilitates to prepare products at a low cost.

For example, compound (I) is administered to patients suffering from acute pulmonary disorders by intravenous drips. The high-dosage product of the present invention alleviates the burden of those engaged in medical care (for example, preparing liquids for injection every several hours before administration, treating plural vials at the same time, etc.).

BEST MODE FOR CARRYING OUT THE PRESENT INVENTION

The following examples illustrate the present invention, but the present invention does not limit to them.

EXAMPLE 1

By the following method, the concentration of compound (I) was measured when compound (I) was completely dissolved in various ratios of mixed solvent comprising water and ethanol.

Experimental Method

Mixed solvent of ethanol and water was prepared so as to fix the ratio of ethanol to be as shown in table 1.

Above mixed solvent was titrated with various added volume for compound (I) and the mixture was vigorously stirred and was left alone for several minutes.

The above operation was done repeatedly until confirming that the solute was completely dissolved by visual recognition.

Solubility A was given by dividing the amount of solute (mg) with the volume of added solvent (ml) when the solute was completely dissolved; and solubility B was given by dividing the amount of solute with the volume of added solvent before the solute was completely dissolved (mg). The results are shown in table 1.

TABLE 1

| ratio of ethanol [vol %] | solute [mg] | titration volume [ml] | total added volume when compound (I) is completely dissolved [ml] | solubility A [mg/ml] | solubility B [mg/ml] |
|---|---|---|---|---|---|
| 0 | 10 | 1 | 45 | 0.22 | 0.23 |
| 10 | 50 | 5 | 60 | 0.83 | 0.91 |
| 15 | 50 | 5 | 55 | 0.91 | 1.00 |
| 20 | 50 | 5 | 35 | 1.43 | 1.67 |
| 25 | 50 | 5 | 30 | 1.67 | 2.00 |
| 30 | 50 | 0.1 | 0.5 | 100.00 | 125.00 |
| 40 | 50 | 0.1 | 0.4 | 125.00 | 166.67 |

TABLE 1-continued

| ratio of ethanol [vol %] | solute [mg] | titration volume [ml] | total added volume when compound (I) is completely dissolved [ml] | solubility A [mg/ml] | solubility B [mg/ml] |
|---|---|---|---|---|---|
| 50 | 50 | 0.1 | 0.3 | 166.67 | 250.00 |
| 60 | 50 | 0.1 | 0.3 | 166.67 | 250.00 |
| 70 | 50 | 0.1 | 0.4 | 125.00 | 166.67 |
| 80 | 50 | 0.1 | 0.4 | 125.00 | 166.67 |
| 90 | 50 | 0.1 | 1 | 50.00 | 55.56 |
| 100 | 50 | 1 | 10 | 5.00 | 5.56 |

It is judged that the solubility of compound (I) to mixed solvent of ethanol and water is between solubility A and solubility B.

EXAMPLE 2

In a mixed solvent of water and ethanol (the ratio of water and ethanol is water 6.5 (weight) vs. ethanol 3.5 (weight)) were dissolved compound (I) (400 mg) and D-mannitol (100 mg) to fix the volume 5 ml in total. The freeze-dried product was prepared using the above solution at −50° C. for 8 hours and at 10 Pa for 20 hours, using the solution. The obtained product was preserved under the accelerated condition of 40° C. and RH 75%, 150 days, and then the residual rate of compound (I) was measured. The results are shown in table 2.

TABLE 2

| Preserving condition | Residual Rate |
|---|---|
| Just after freeze-drying process was finished | 100% |
| 40° C., RH 75% for 150 days | 99.9% |

As shown in table 2, the freeze-dried product of the present invention is stable enough even in a severe condition.

EXAMPLE 3

Assuming the scene of administration, the stability of the freeze-dried product of the present invention was measured when it was solved in a parenteral solution. To the freeze-dried product which was prepared in example 2 was added a 0.06 N aqueous solution of sodium hydroxide (10 ml). Compound (I) was dissolved quickly to give a clear solution. The pH value just after preparation and the residual rate of compound (I) is more than 98.5%, then it was confirmed that the solution is stable enough.

The invention claimed is:

1. A method for improving the solubility of the compound of formula (I):

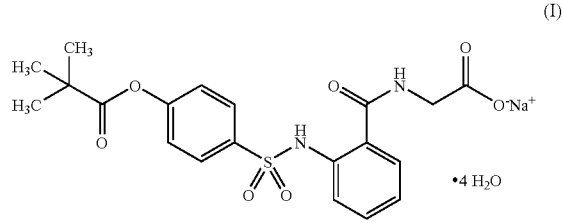

comprising dissolving the compound in a mixed solvent of water and ethanol, wherein the ratio of ethanol/water is 3.0/7.0-4.0/6.0 (v/v).

* * * * *

UNITED STATES PATENT AND TRADEMARK OFFICE
CERTIFICATE OF CORRECTION

PATENT NO. : 7,262,317 B2  Page 1 of 1
APPLICATION NO. : 10/333354
DATED : August 28, 2007
INVENTOR(S) : Akira Takada It is certified that error appears in the above-identified patent and that said Letters Patent is hereby corrected as shown below:

Title Pg, Item (73) Assignee: please delete in its entirety and replace with

--Ono Pharmaceutical Co., Ltd., Osaka, Japan--

Signed and Sealed this

Eighth Day of April, 2008

JON W. DUDAS
*Director of the United States Patent and Trademark Office*